US008114657B2

(12) United States Patent
Lawman et al.

(10) Patent No.: US 8,114,657 B2
(45) Date of Patent: Feb. 14, 2012

(54) ANTIMICROBIAL PROTEIN COMPOSITIONS AND PRODUCTION THEREOF FROM MARINE BACTERIA

(75) Inventors: Michael Lawman, Tampa, FL (US); Selena Braccili, San Diego, CA (US); Shabnam Eidizadeh, Lutz, FL (US)

(73) Assignee: St. Joseph' Children' Hospital, Tampa, FL (US)

( * ) Notice: Subject to any disclaimer, the term of this patent is extended or adjusted under 35 U.S.C. 154(b) by 0 days.

(21) Appl. No.: 13/060,448

(22) PCT Filed: Aug. 24, 2009

(86) PCT No.: PCT/US2009/054766
§ 371 (c)(1),
(2), (4) Date: Feb. 24, 2011

(87) PCT Pub. No.: WO2010/027736
PCT Pub. Date: Mar. 11, 2010

(65) Prior Publication Data
US 2011/0160124 A1    Jun. 30, 2011

Related U.S. Application Data

(60) Provisional application No. 61/159,128, filed on Mar. 11, 2009, provisional application No. 61/091,535, filed on Aug. 25, 2008.

(51) Int. Cl.
*A61K 38/16* (2006.01)
(52) U.S. Cl. ............... 435/252.4; 435/252.1; 514/2.7; 514/2.3

(58) Field of Classification Search ............... None
See application file for complete search history.

(56) References Cited

U.S. PATENT DOCUMENTS

| | | | | |
|---|---|---|---|---|
| 4,027,014 A | * | 5/1977 | Ezaki et al. | 424/122 |
| 6,376,548 B1 | * | 4/2002 | Mulvihill et al. | 514/615 |
| 2003/0135032 A1 | * | 7/2003 | Lewis et al. | 536/23.1 |
| 2006/0147410 A1 | * | 7/2006 | Qian et al. | 424/78.09 |
| 2006/0233845 A1 | * | 10/2006 | Lukowski et al. | 424/401 |
| 2008/0090900 A1 | * | 4/2008 | Ahmed et al. | 514/461 |
| 2008/0318790 A1 | * | 12/2008 | Ebneth et al. | 504/307 |

OTHER PUBLICATIONS

Desjardine, K. et al. "Tauramamide, a Lipopeptide Antibiotic Produced in Culture by *Brevibacillus laterosporus* Isolated from a Marine Habitat: Structure Elucidation and Synthesis" *Journal of Natural Products*, 2007, pp. 1850-1853, vol. 70, No. 12.

Matsuo, Y. et al. "Urukthapelstatin A, a Novel Cytotoxic Substance from Marine-derived *Mechercharimyces asporophorigenens* YM11-542" *The Journal of Antibiotics*, 2007, pp. 251-255, vol. 60, No. 4.

(Continued)

*Primary Examiner* — Albert Navarro
*Assistant Examiner* — Ginny Portner
(74) *Attorney, Agent, or Firm* — Saliwanchik, Lloyd & Eisenschenk (57) ABSTRACT

Several bacterial species were isolated from marine segment obtained from seabed sediment at depths exceeding 1700 feet. At least four of the bacteria produced a compound that showed antibacterial activity against one or more multiple-drug-resistant (MDR) bacteria isolated from hospitals and clinics. One isolate, SJCH-12, exhibited a broad range of activity against MDR strains tested, including methicillin resistant *Staphylococcus aureus* (MRSA).

4 Claims, 8 Drawing Sheets

OTHER PUBLICATIONS

Oku, N. et al. "Unnarmicins A and C, New Antibacterial Depsipeptides Produced by Marine Bacterium *Photobacterium* sp. MBIC06485" *The Journal of Antibiotics*, 2008, pp. 11-17, vol. 61, No. 1.

Oku, N. et al. "Ariakemicins A and B, Novel Polyketide-peptide Antibiotics from a Marine Gliding Bacterium of the Genus *Rapidithrix*" *Organic Letters*, 2008, pp. 2481-2484, vol. 10, No. 12.

Acebal, C. et al. "Agrochelin, a New Cytotoxic Antibiotic from a Marine *Agrobacterium*, Taxonomy, Fermentation, Isolation, Physico-chemical Properties and Biological Activity" *The Journal of Antibiotics*, Nov. 1999, pp. 983-987, vol. 52, No. 11.

Biabani, M. A. et al. "δIndomycinone: A New Member of Pluramycin Class of Antibiotics Isolated from Marine *Streptomyces* sp." *The Journal of Antibiotics*, Oct. 1997, pp. 874-877, vol. 50, No. 10.

Gauthier, G. et al. "Phylogenetic Analysis of the Genera *Alteromonas, Shewanella*, and *Moritella* Using Genes Coding for Small-Subunit rRNA Sequences and Division of the Genus *Alteromonas* into Two Genera, *Alteromonas* (Emended) and *Pseudoalteromonas* gen. nov., and Proposal of Twelve New Species Combinations" *International Journal of Systematic Bacteriology*, Oct. 1995, pp. 755-761, vol. 45, No. 4.

Imamura, N. et al. "New Anticancer Antibiotics Pelagiomicins, Produced by a New Marine Bacterium *Pelagiobacter variabilis*" *The Journal of Antibiotics*, Jan. 1997, pp. 8-12, vol. 50, No. 1.

Isnansetyo, A. et al. "MC21-A, a Bactericidal Antibiotic Produced by a New Marine Bacterium, *Pseudoalteromonas phenolica* sp. nov. O-BC30$^T$, against Methicillin-Resistant *Staphylococcus aureus*" *Antimicrobial Agents and Chemotherapy*, Feb. 2003, pp. 480-488, vol. 47, No. 2.

Pusecker, K. et al. "Dihydrophencomycin Methyl Ester, a New Phenazine Derivative from a Marine *Streptomycete*" *The Journal of Antibiotics*, Jun. 1997, pp. 479-483, vol. 50, No. 6.

Usdin, S. "Ketek politics" *BioCentury The Bernstein Report*, Jun. 26, 2006, pp. 1-6, vol. 14, No. 28.

Hughes, C. C. et al. "The Marinopyrroles, Antibiotics of an Unprecedented Structure Class from a Marine *Streptomyces* sp." *Organic Letters*, 2008, pp. 629-631, vol. 10, No. 4.

Chemistry & Engineering News, Jan. 28, 2008, p. 57.

\* cited by examiner

2-D Gel of Bacterial Lysate (SCH-12)

FIG. 4

Properties of SCH-12 Bacterium

16S rRNA gene sequence analysis (PCR Amplified)

```
   1 TTTGATCCTG GCTCAGATTG AACGCTGGCG GCAGGCCTAA CACATGCAAG TCGAACGTA
  61 ACAGGAANCA GCTTGCTGNT TCGCTGACGA GTGGCGGACG GGTGAGTAAT GTCTGGGAAA
 121 CTGCCTGATG GAGGGGGATA ACTACTGGAA ACGGTAGCTA ATACCGCATA ACGTCGCAAG
 181 ACCAAAGAGG GGGACCTTCG GGCCTCTTGC CATCGGATGT GCCCAGATGG GATTAGCTAG
 241 TAGGTGGGGT AAAGGCTCAC CTAGGCGACG ATCCCTAGCT GGTCTGAGAG GATGACCAGC
 301 CACACTGGAA CTGAGACACG GTCCAGACTC CTACGGGAGG CAGCAGTGGG GAATATTGCA
 361 CAATGGGCGC AAGCCTGATG CAGCCATGCC GCGTGTATGA AGAAGGCCTT CGGGTTGTAA
 421 AGTACTTTCA GCGGGGAGGA AGGGAGTAAA GTTAATACCT TTGCTCATTG ACGTTACCCG
 481 CAGAAGAAGC ACCGGCTAAC TCCGTGCCAG CAGCCGCGGT AATACGGAGG GTGCAAGCGT
 541 TAATCGGAAT TACTGGGCGT AAAGCGCACG CAGGCGGTTT GTTAAGTCAG ATGTGAAATC
 601 CCCGGGCTCA ACCTGGGAAC TGCATCTGAT ACTGGCAAGC TTGAGTCTCG TAGAGGGGGG
 661 TAGAATTCCA GGTGTAGCGG TGAAATGCGT AGAGATCTGG AGGAATACCG GTGGCGAAGG
 721 CGGCCCCCTG GACGAAGACT GACGCTCAGG TGCGAAAGCG TGGGGAGCAA ACAGGATTAG
 781 ATACCCTGGT AGTCCACGCC GTAAACGATG TCGACTTGGA GGTTGTGCCC TTGAGGCGTG
 841 GCTTCCGGAG CTAACGCGTT AAGTCGACCG CCTGGGGAGT ACGGCCGCAA GGTTAAAACT
 901 CAAATGAATT GACGGGGGCC CGCACAAGCG GTGGAGCATG TGGTTTAATT CGATGCAACG
 961 CGAAGAACCT TACCTGGTCT TGACATCCAC GGAAGTTTTC AGAGATGAGA ATGTGCCTTC
1021 GGGAACCGTG AGACAGGTGC TGCATGGCTG TCGTCAGCTC GTGTTGTGAA ATGTTGGGTT
1081 AAGTCCCGCA ACGAGCGCAA CCCTTATCCT TTGTTGCCAG CGGTCCGGCC GGGAACTCAA
1141 AGGAGACTGC CAGTGATAAA CTGGAGGAAG GTGGGGATGA CGTCAAGTCA TCATGGCCCT
1201 TACGACCAGG GCTACACACG TGCTACAATG GCGCATACAA AGAGAAGCGA CCTCGCGAGA
1261 GCAAGCGGAC CTCATAAAGT GCGTCGTAGT CCGGATTGGA GTCTGCAACT CGACTCCATG
1321 AAGTCGGAAT CGCTAGTAAT CGTGGATCAG AATGCCACGG TGAATACGTT CCCGGGCCTT
1381 GTACACACCG CCCGTCACAC CATGGGAGTG GGTTGCAAAA GAAGTAGGTA GCTTAACCTT
1441 CGGGAGGGCG CTTACCACTT TGTGATTCAT GACTGGGGTG AGTCGTAAC AAGGTAACCG
1501 TAGGGGAACC TGCGGCTGGA TCACCTCCTT
``` strain SJCH-12 (ID 08-1083):
may represent a new species within the enterobacteriaceae.

- Shape of cells: Rods
- Width (um): 0.7-0.8
- Length (um): 1.2-2.5
- Motile
- Gram negative
- Anaerobic (facultative)
- Acid producer (ASS)
- pigment producing (orange)
- hemolysin (+/-)
- No plasmid detected

FIG. 5

SJCH-12

FIG. 8
Antimicrobial Activity of 08-1083 From the SCH-12 Isolate

ANTIMICROBIAL PROTEIN COMPOSITIONS AND PRODUCTION THEREOF FROM MARINE BACTERIA

CROSS REFERENCE TO RELATED APPLICATIONS

This application is the U.S. national stage application of International Patent Application No. PCT/US2009/054766, filed Aug. 24, 2009, which claims the benefit of U.S. Provisional Application Ser. No. 61/091,535, filed Aug. 25, 2008, and Ser. No. 61/159,128, filed Mar. 11, 2009, the disclosures of which are hereby incorporated by reference in their entirety, including all figures, tables and amino acid or nucleic acid sequences.

BACKGROUND OF THE INVENTION

1. Field of the Invention

The invention relates generally to polypeptide antibiotics produced by bacteria isolated from marine environments. In particular, the present invention is directed to antibacterial compositions useful for treating a broad spectrum of bacterial infections.

2. Description of Background Art

The search for new and advanced cancer treatments is dependent upon the discovery of new compounds, the development of new therapeutic strategies and advances in predictive models for disease. Due to the immense technical advances that have been made in the pharmaceutical industry and medicine, there is a resurging interest in the use of natural products in the formulation of therapeutic drugs. In fact, many of the drugs in use today are derivatives of natural products, which provide additional incentive to take further advantage of the biodiversity available for the discovery of new drugs, particularly in the area of cancer therapy.

In response to evolutionary pressures imposed over time, new molecules and compounds constantly evolve, resulting in a structural diversity against which modern technologies such as combinatorial chemistry cannot compete. To make use of the biological and chemical diversity of natural products, it has become increasingly clear that the most powerful approach in the search for new drugs begins with drug leads revealed by natural product-based drug discovery techniques, and subsequently utilizing genomic-based platforms to identify and produce the lead compounds that are the basis for next generation drugs.

Since the discovery of penicillin in 1929, nearly 50,000 natural products have been isolated from microorganisms. Over 10,000 of these compounds have been shown to have biological activity and 100 of these are in use today in the treatment of a wide range of human and animal diseases. Numerous antibiotics and anticancer agents have been identified and have provided a powerful weapon in the arsenal of drugs for treating infectious diseases.

Microbes, unfortunately, constantly adapt to changing environments so that multiple drug resistance develops rapidly after infectious microorganisms are exposed to new antimicrobial agents. This resistance poses a continuing challenge to identify new agents that will effectively control bacterial growth and propagation.

A majority of antibiotics have, like penicillin, been isolated from natural sources or derived from bioactive natural products. The list is extensive and includes β-lactam antibiotics such as the cephalosporin family, chloramphenicol, vancomycin, bacitracin and structurally diverse compounds such as brominated pyrroles, magnesidins, and substituted biphenyldiols. The sources of these compounds are equally diverse and range from soil bacteria to marine pseudomonads and bioflora.

The oceans of the world cover over 70% of the earth's surface and have been described as being the "mother of the origin of life." Given the uniqueness of the environment found in the oceans at various geographic locations around the world, organisms have responded by developing the structurally unique natural compounds required for adaptation and survival in a marine environment. Many of these compounds show pharmacologic activity against many human illnesses, ranging from infectious diseases to cancers. Previously discovered life saving drugs and potentially new drugs have been and are being isolated from microorganisms, algae, plants and invertebrates. With the advent of the technological advances made in the biotechnology, biomedical and pharmaceutical arenas, the discovery of new therapeutics from aquatic organisms has become a "new science". Of the 25,000 plant species classified to date, only 10% have been studied in attempts to discover new therapeutically active compounds.

Marine environments have been even less utilized as sources of new drugs. Over 80% of the world's plant and animal species are found in a marine environment. Of the 34 fundamental phyla representing life, 17 occur on land whereas 32 occur in the ocean. As of 2004, basic research has led to the isolation of approximately 14,000 marine natural products with approximately 10-15 different natural products entering clinical testing (FDA sponsored clinical trials) in the cancer, infectious disease, pain and inflammatory disease fields Despite recognition that the marine environment is an exceptional reservoir of bioactive natural products arising from an amazing diversity of life, the identification of potential new drugs from the oceans has progressed only slowly. Bioactive compounds have been extracted from a variety of marine organisms: tunicates, sponges, soft corals, sea hares, nudibranchs, bryozoans, sea slugs and microorganisms. Spongouridine and spongothymidine from the Caribbean sponge were among the first bioactive compounds isolated over fifty years ago.

Drug research studies on sponge-derived products has led to the development of anticancer and antiviral compounds. Two successfully launched marine organism-derived (or analog derived) products reaching the clinics within the last 30 years are Acyclovir (synthetically known as Ara A) and cephalosporin. Synthetic Ara A was modeled on the previously isolated sponge-derived spongothymidine or spongouridine and later isolated as a natural product from *Eunicella cavolini*. The antibiotic mimosamycin was isolated from a nudibranch sea slug and also found in certain sponges.

Secondary metabolites of marine organisms have also been studied over the past decades, which have often exhibited unique structures. Between 2000 and 2005, ziconotide, aplidine, KRN7000, discodermolide, bryostatin, synthadotin, dolastatin 10, soblidotin, halichondrin, HTI-286, kahalalide F, spisulosine, squalamine and ecteinascidin 743 have been identified from marine sources as potential drug candidates (Butler, 2005; Newman and Cragg, 2004A; Newman and Cragg, 2004B.) Several of these compounds are or have been in clinical trials.

Ziconotide, a 24-27 amino acid peptide from the -conotoxin cyclic cysteine known family, was identified from cone snail (*Conus magnus*) venom. It is a novel non-opioid analgesic that blocks the N-type voltage gated channel and was developed for management of severe chronic pain.

Aplidine is an analog of the didemnins isolated from *Aplidium albicans*, a Mediterranean tunicate, and is reported to show activity against medullary thyroid carcinoma, renal carcinoma, melanoma and tumors of neuroendocrine origin and to inhibit secretion of vascular endothelial growth factor (VEGF) (Taraboletti, 2004).

Agelasphins are new glycosphingolipids isolated as antitumor agents from *Agelas mauritianus*, an Okinawan sponge. KRN7000 is a synthetic derivative in clinical trials whose activity is attributed to natural killer cell activation effected as a ligand of VαT cell antigen receptor (Hayakawa, et al., 2003).

Bryostatin was isolated from *Bulgula neritina* and binds to the same receptors as phobol esters but differs in not having any tumor promoting activity. Binding of bryostatin down-regulates protein kinase C isoforms in several tumor cells, causing inhibition of growth, alteration of differentiation and/or cell death (Newman, 2005).

Discodermolide has been isolated from *Discodermia* dissolute and found to inhibit tumor cell growth in vitro (Capon, 2001) as do dolastatins, which are linear peptides isolated from the Indian Ocean sea hare *Dolabela auricularia* (Pettit, et al., 1989).

Other potential drugs have been isolated from marine sources, some of which are in or are candidates for clinical trial studies. Table 1 is a list of examples of additional compounds recovered from marine environments and the organism from which it was isolated.

TABLE 1

| DRUG | SOURCE | ORGANISM |
|---|---|---|
| Halichondrin E7389 | | *Halichondria okadai* |
| HTI-286 | sponge | *Hemiasterella minor* |
| Kahalalide F | mollusk | *Elysia rufescens* |
| Spisulosine | | *Spisula polynyma* |
| Squalamine | dogfish shark | *Squalus acanthias* |
| Ecteinascidin | marine tunicate | *Ecteinascidia turbinate* |

The vast majority of compounds currently in clinical trials or being considered as potential drug candidates exhibit antitumor activity, although the search for other classes of drugs has currently produced far fewer candidates.

Marine microorganisms have produced several potential antimicrobials, and new antibiotics isolated over the past several years, include lololatin, agrochelin (Acebal, et al., 1999) and sesbanimides from agrobacterium, pelagiomicins from *Pelagiobacter variabilis*, d-indomycinone from a *Streptomyces* sp. (Biabini, et al., 1997) and dihydrophencomycin from *Streptomyces* (Pusecker, et al., 1997). *Pseudoalteromonas Alteromonas* has also been reported to produce antibiotics and other bioactive substances (Gauthier, et al., 1995).

Marine sources historically have been underutilized in the search for new drugs and are only now being more fully exploited by interdisciplinary groups devoted solely to drug discovery research. Despite some progress in identifying new antimicrobial compounds, there are a limited number of marine-derived compounds that are active against MDR bacteria. In 2005, only 6 new anti-bacterial pharmaceuticals were reported to be in the development pipeline (Usdin, 2006).

Recently, an unusual pair of antibiotics isolated from bacteria obtained from ocean sediments have been identified by Fenical, et al. (2008). The new compounds have a basic pyrrole structure that is an N, C2-linked bispyrrole, and exhibit antimicrobial activity against methicillin-resistant *S. aureus*.

The rapid increase in the number of MDR strains and the decreasing effectiveness of currently used antimicrobials, are strong indications of the need for new and effective first-generation antibiotics.

SUMMARY OF THE INVENTION

The present invention provides antibacterial compositions based on novel compounds obtained from marine sources. Several different antibiotic activities were identified in samples provided from core seabed samples on the bottom of the Atlantic Ocean. The samples were retrieved near the shipwreck of the SS Republic lost in a hurricane on Oct. 25, 1865, which sank approximately 100 miles off the Georgia coast and was found nearly a century later on the seabed at approximately 518 meters depth.

The active compounds produced by the isolated marine bacteria are relatively small proteins with molecular weights in the range of 5 kDa. They appear to be produced by several species of bacteria.

Thirteen bacterial isolates were isolated from the marine sediment samples of which four had antibacterial activity (SJCH-3, 10, 11 and 12); however, only SJCH-12 exhibited a broad range of antibacterial activity and only SJCH-12 had high activity against MRSA.

Bacterial isolate SJCH-12 was found to comprise two bacteria, one of which appeared to be a pseudomonad, tentatively identified as a *Pseudomonas stutzeri* species while the other, also a gram negative rod was similar to *Shigella* or an *E. coli* genus. The antibacterial polypeptide produced by the SJCH-12 culture may have required the presence of both bacteria but it was not determined whether or not actually produced by a single species.

DETAILED DESCRIPTION OF THE INVENTION

The present invention provides novel polypeptide compositions that show a wide range of antibacterial activity. The active compounds were isolated from marine bacteria isolated from core sample sediments which included coarse brown sediment with worm casings visible (core sample 1);

rocky with grey sediment (core sample 2); and grey sediment containing rock-like material (core sample 3). Bacterial colonies were isolated from these samples. Of 13 bacterial colonies, at least 1 putative new species of bacterium was isolated and 2 bio-activities identified, one of which was a highly antimicrobial peptide identified as 08-1083 and the other an unidentified compound with adhesive properties. Of 93 core sample extracts, 20 active compounds were indicated in in vitro Tox. A Assays.

Eleven samples were taken from the three core samples and plated on LB agar or grown in LB broth. Thirteen bacterial isolates were colony purified and identified as SJCH 1-13. Of the 13 isolates, 4 exhibited antimicrobial activity. SJCH-12 isolate showed activity against 8 of 11 organisms tested, while SJCH-11 exhibited activity against 3 of the organisms; SJCH-10 against two; and SJCH-3 against only one, see Table 2.

EXAMPLES

Materials and Methods

Marine seabed samples were obtained from an Odyssey Dive Site located in the Atlantic ocean approximately 100 miles east of the Georgia coastline. Samples comprised seabed material recovered by Odyssey Marine Exploration (Tampa, Fla.) remote operated vehicle during routine dive operations at 1700 feet. Samples were stored at 4° C. or ambient temperature prior to analysis.

Bacteria isolate SJCH-12 was deposited on Oct. 20, 2008 at the Deutsche Sammlung von Mikroorganismen und Zellkulturen GmbH, Inhoffenstrasse 7B, 38124 Braunschweig, Germany)Germany under the conditions of the Budapest Treaty and assigned accession number DSM 21971.

The following examples are provided as illustrations of the invention and are in no way to be considered limiting.

Materials and Methods

Bacterial cultures were grown and isolated under standard conditions on agar or in LB medium.

Example 1

Isolation of Bacterial Colonies

A total of 13 isolates were obtained. These are listed in Table 2. Of these, isolates SJCH-10, SJCH-11, SJCh-12 and SJCH-13 exhibited antibacterial activity of varying degrees against one or more of the multi-drug resistant (MDR) bacterial strains, *K. pneumoniae, K. Oxytoca* and *A. baumannii* as shown in Table 3 in Example 2.

TABLE 2

| STRAIN |
| --- |
| *Aeromonas hydrophila* |
| *Staphylococcus aureus* |
| *Escherichia coli* |
| *Enterobacter aerogenes* |
| *Proteus vulgaris* |
| *Klebsiella pneumoniae* |
| *Providencia alcalifaciens* |
| *Klebsiella oxytoca* |
| *Acinetobacter baumannii* |
| *Serratia liquefaciens* |
| *Pseudomonas aeruginosa* |

Example 2

Antibacterial Activity of 13 Bacteria Isolates

Isolates selected from the bacterial colonies in Example 1 were tested for antibacterial activity against several strains of bacteria listed in Table 2 and isolated from hospital surgical suites and patient wards, including multi-drug resistant (MDR) strains. The MDR strains are *Klebsiella pneumoniae* (KP), *Klebsiella oxytoca* (KO) and *Acinetobacter baumannii* (AB). Antibacterial activities are shown in Table 3.

TABLE 3

Antibiotic Sensitivity Assay
Marine Bacterial Isolates

| Bacterial Strains | SJCH-1 | SJCH-2 | SJCH-3 | SJCH-5 | SJCH-7 | SJCH-8 | SJCH-9 | SJCH-10 | SJCH-11 | SJCH-12 | SJCH-13 |
| --- | --- | --- | --- | --- | --- | --- | --- | --- | --- | --- | --- |
| AH | Neg | Neg | Neg | Neg | Neg | Neg | Neg | Neg | Neg | Neg | Neg |
| MRSA | Neg | Neg | Neg | Neg | Neg | Neg | Neg | Neg | +/− | Neg | Neg |
| EC | Neg | Neg | Neg | Neg | Neg | Neg | Neg | Neg | Neg | + | Neg |
| EA | Neg | Neg | Neg | Neg | Neg | Neg | Neg | Neg | Neg | + | Neg |
| PV | Neg | Neg | Neg | Neg | Neg | Neg | Neg | Neg | Neg | + | Neg |
| KP | Neg | Neg | + | Neg | Neg | Neg | Neg | + | + | + | Neg |
| PA | Neg | Neg | Neg | Neg | Neg | Neg | Neg | Neg | Neg | Neg | Neg |
| KO | Neg | Neg | Neg | Neg | Neg | Neg | Neg | + | + | + | Neg |
| AB | Neg | Neg | Neg | Neg | Neg | Neg | Neg | Neg | Neg | + | +/− |
| SL | Neg | Neg | Neg | Neg | Neg | Neg | Neg | Neg | Neg | Neg | Neg |
| PSA | Neg | Neg | Neg | Neg | Neg | Neg | Neg | Neg | Neg | + | Neg |

AH = *Aeromonas hydrophila*
SA = *Staphylococcus aureus*
EC = *E. coli*
EA = *Enterobacter aerogenes*
PV = *Proteus vulgaris*
KP = *Klebsiella pneumoniae*
PA = *Providencia alcalifaciens*
KO = *Klebsiella oxytoca*
AB = *Acinetobacter baumannii*
SL = *Serratia liquefaciens*
PSA = *Pseudomonas aeruginosa*

Example 3

The bacteria from which antibacterially active 08-1083 was isolated were highly adherent when cultured on agar plates. No determination was made as to whether this was an immobilization phenomenon or the result of chemical bonding. Agar is a polymannuronic acid formed as a polymer of agarobiose, composed of disaccharide units of D-galactose and 3,6-anhydro-L-galactose. Agar is commonly used as a cell immobilization medium which allows trapped cells to grow while entrapped in a microporous membrane.

Figure 1:
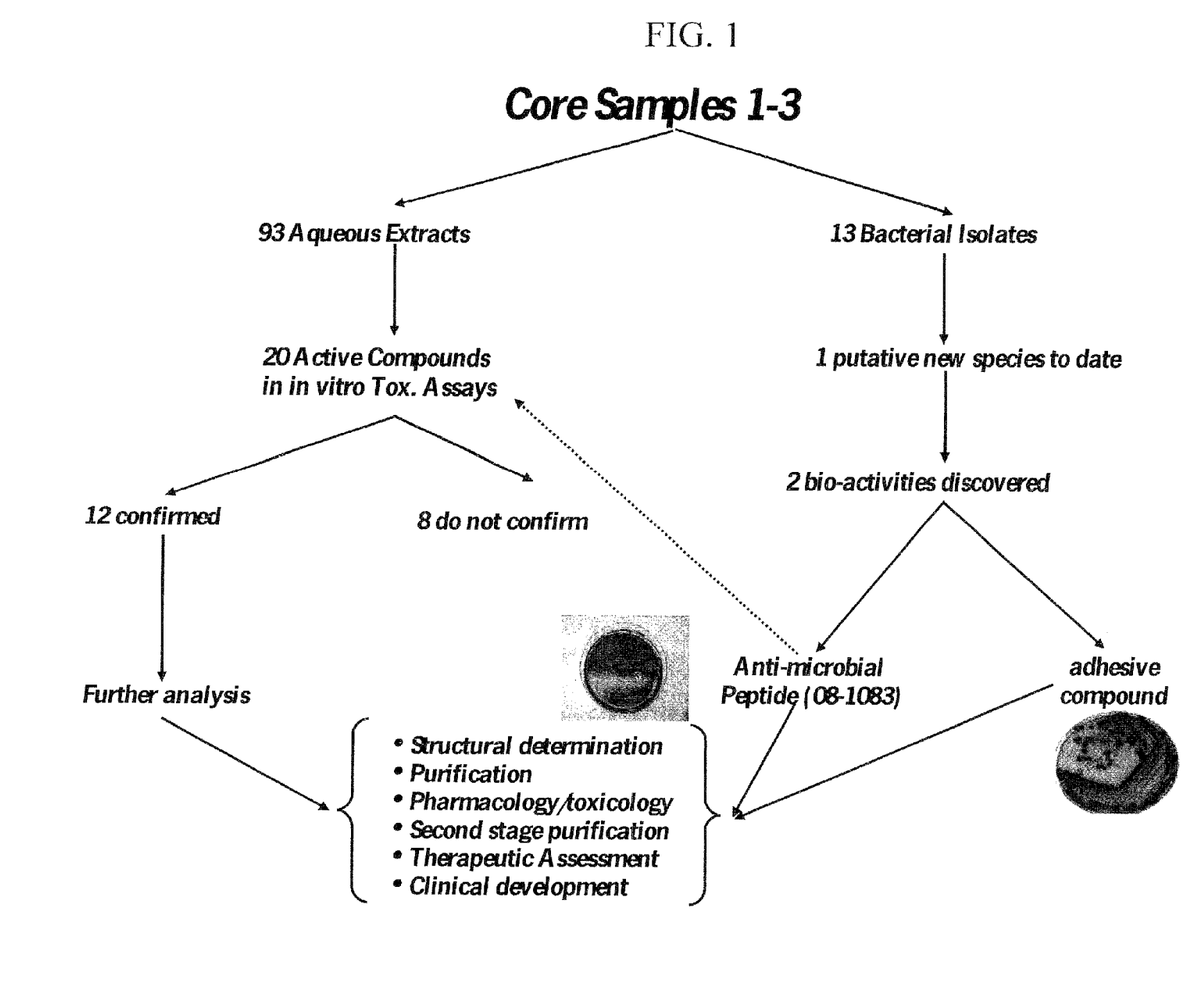
FIG. 1 illustrates the overall process used for isolating the marine microorganisms.
Figure 2:
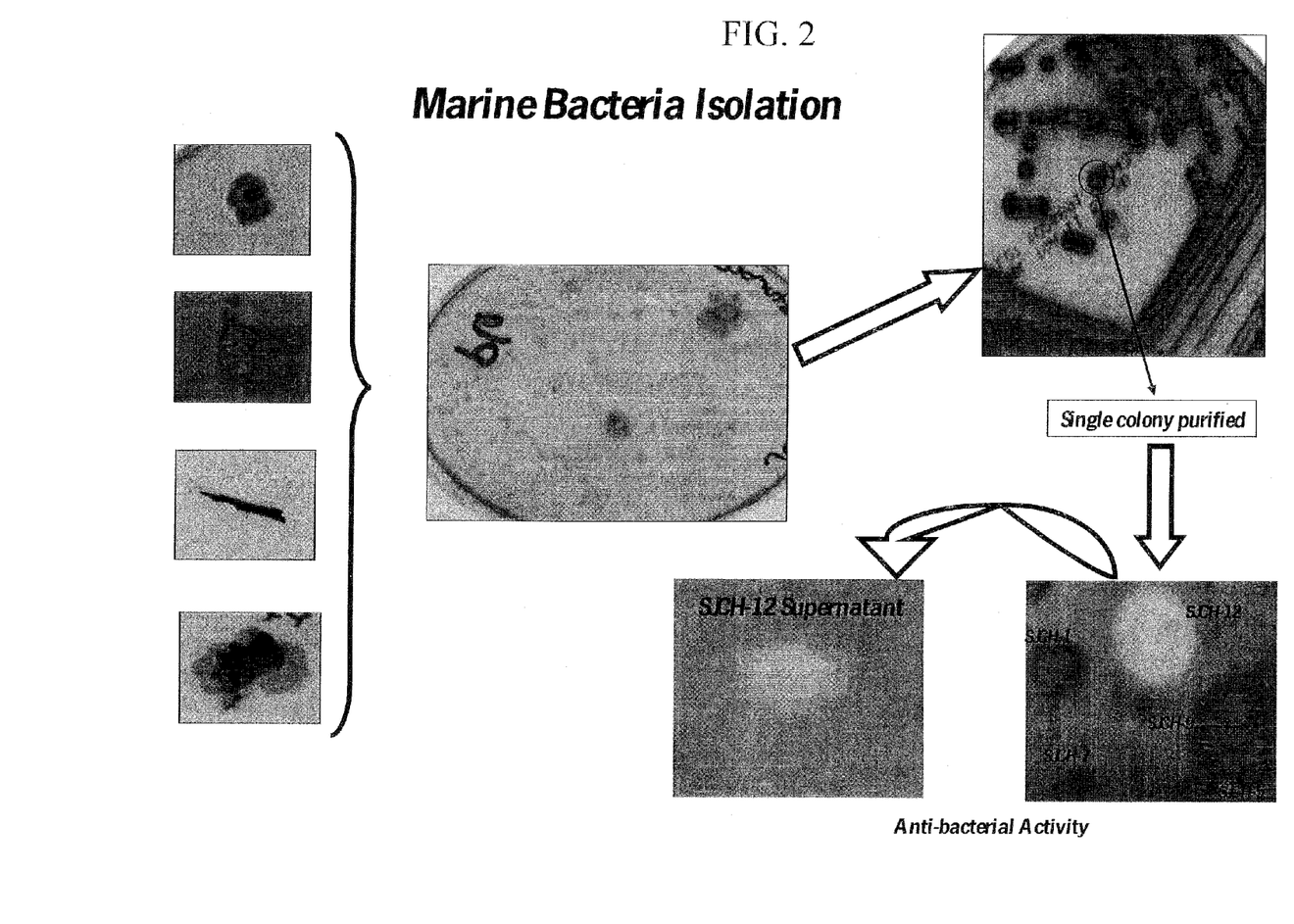
FIG. 2 shows the antibiotic activity of protein 08-1083 in the isolate from marine organism SJCH-12 separated by SDS-gel electrophoresis of soluble SJCH-12 proteins.
Figure 3:
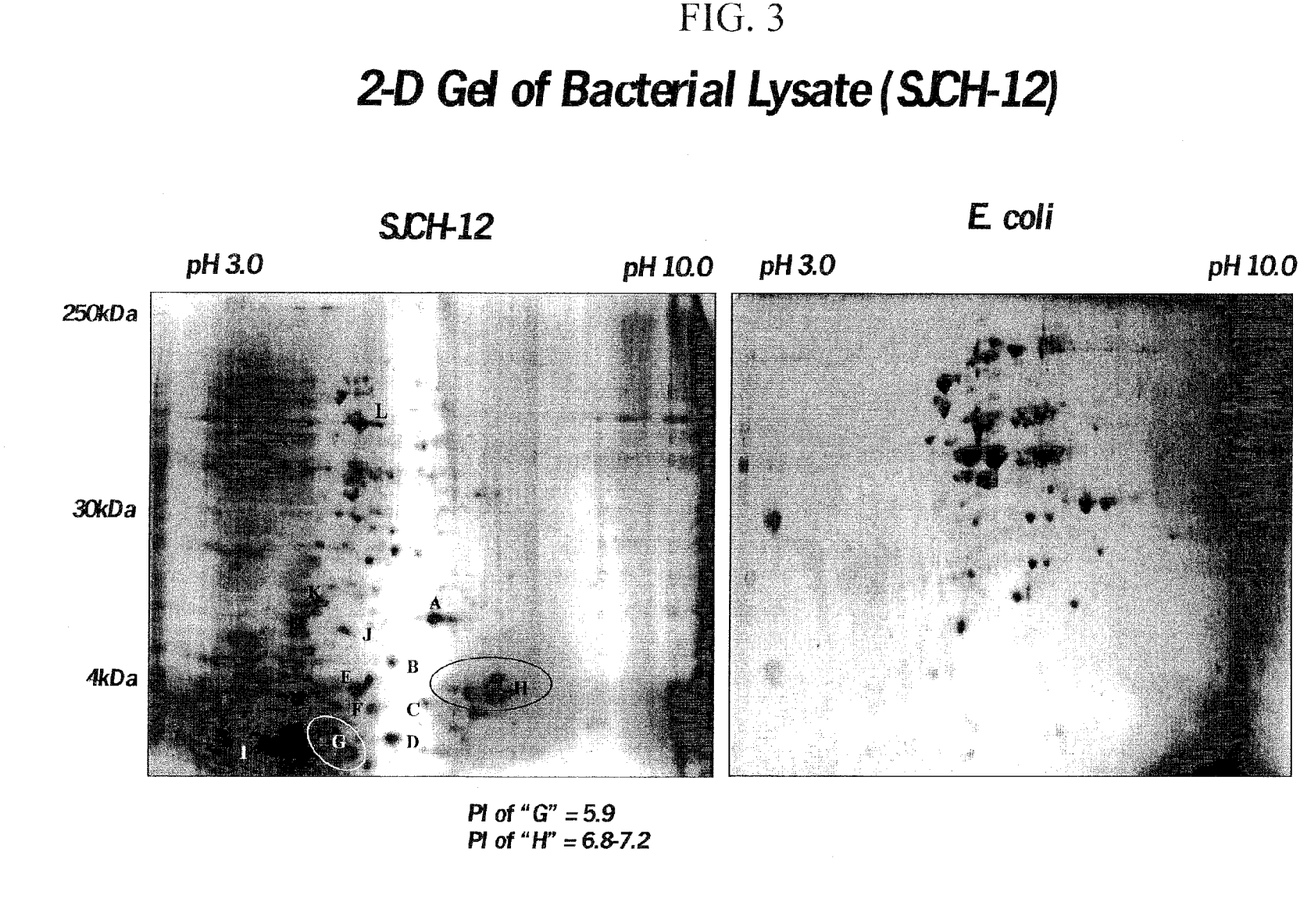
FIG. 3 is a PAGE gel electrophoresis demonstrating the protein profile of the antibiotically active agent in bacterial lysate SJCH-12 on a 16% acrylamide gel. The location of spots G and H having respective measured pIs of 5.9 and 6.8-7.2 is shown in FIG. 4.
Figure 4:
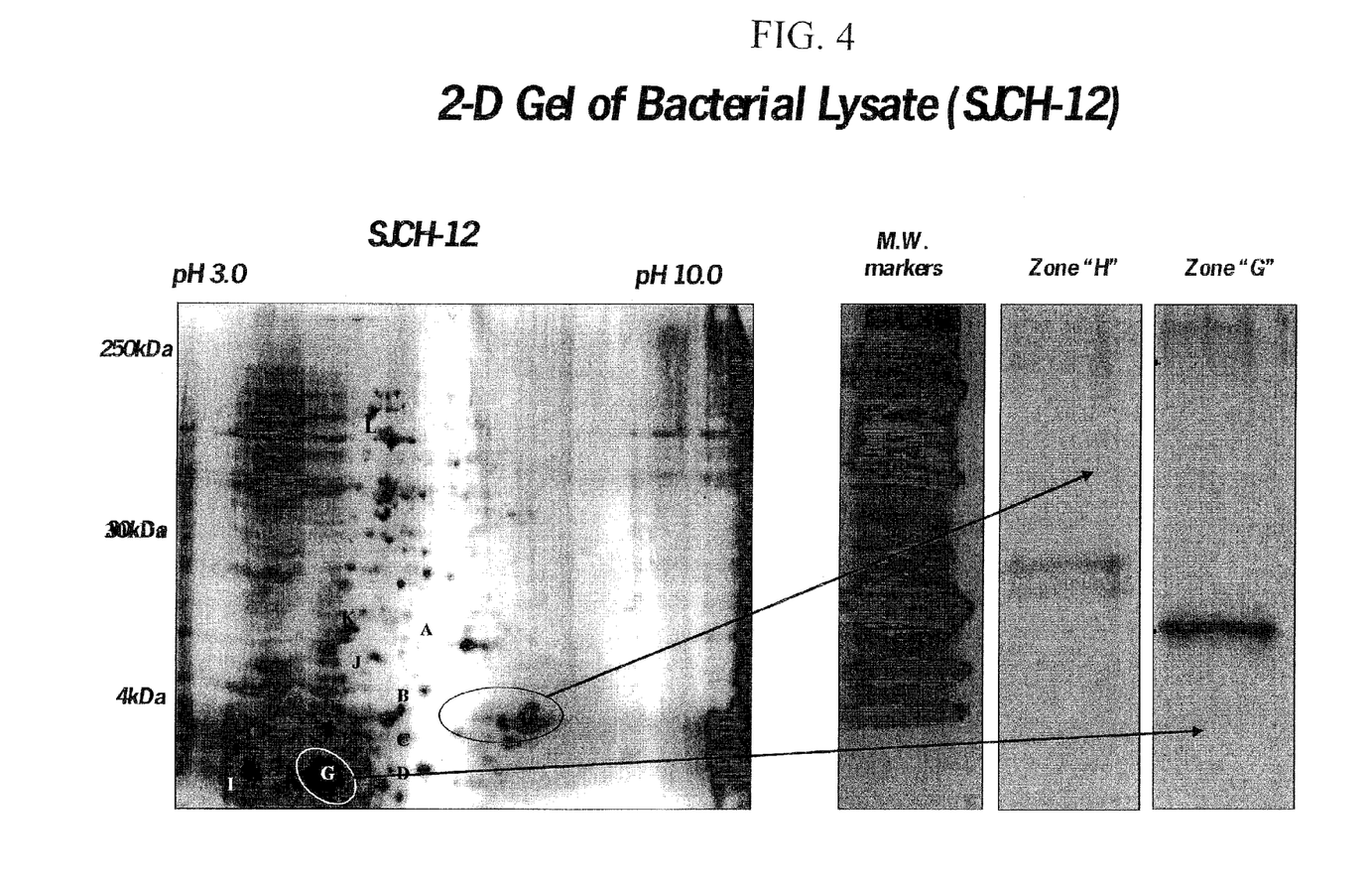
FIG. 4 is a two dimensional gel electrophoresis of the SJCH-12 bacterial lysate. Zone H is shown in FIG. 3 as the corresponding spot with a pI of 6.8-7.2. Zone G is shown in FIG. 3 as having a measured pI of 5.9.
Figure 5:
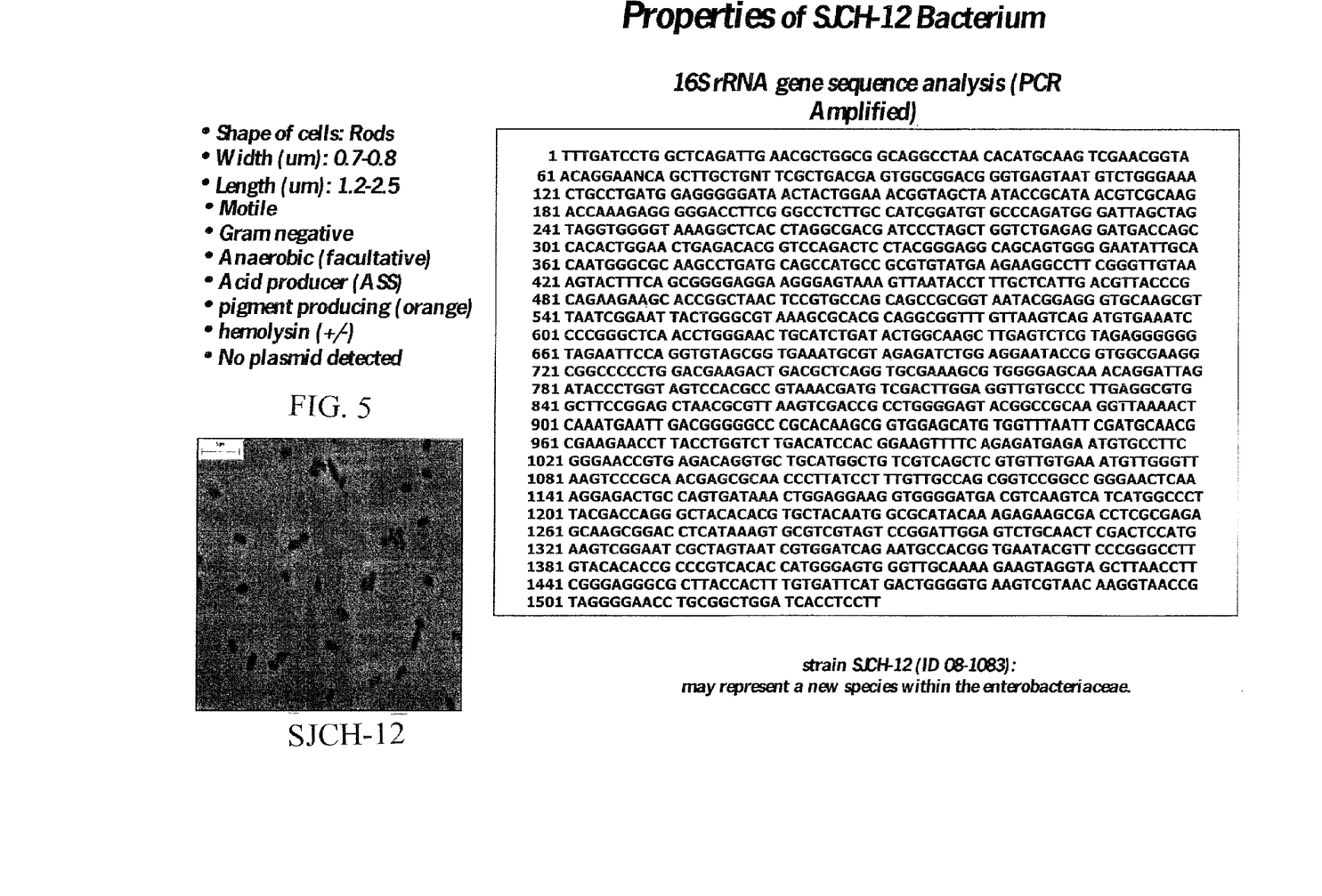
FIG. 5 is a photograph of SJCH-12 bacterium showing the rod shape and the 16SrRNA gene sequence (SEQ ID NO:1) of strain SJCH-12.
Figure 6:
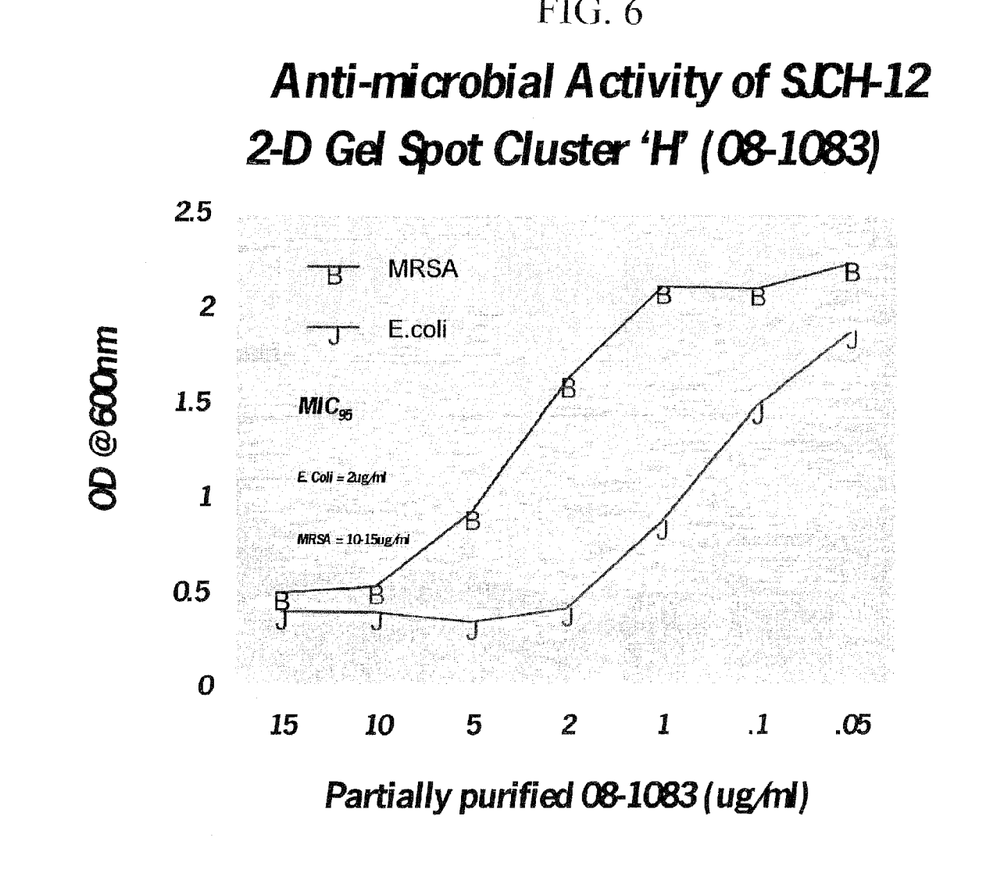
FIG. 6 shows the activity of partially purified protein 08-1083 from bacteria SJCH-12 against MRSA and *E. coli*.
Figure 7:
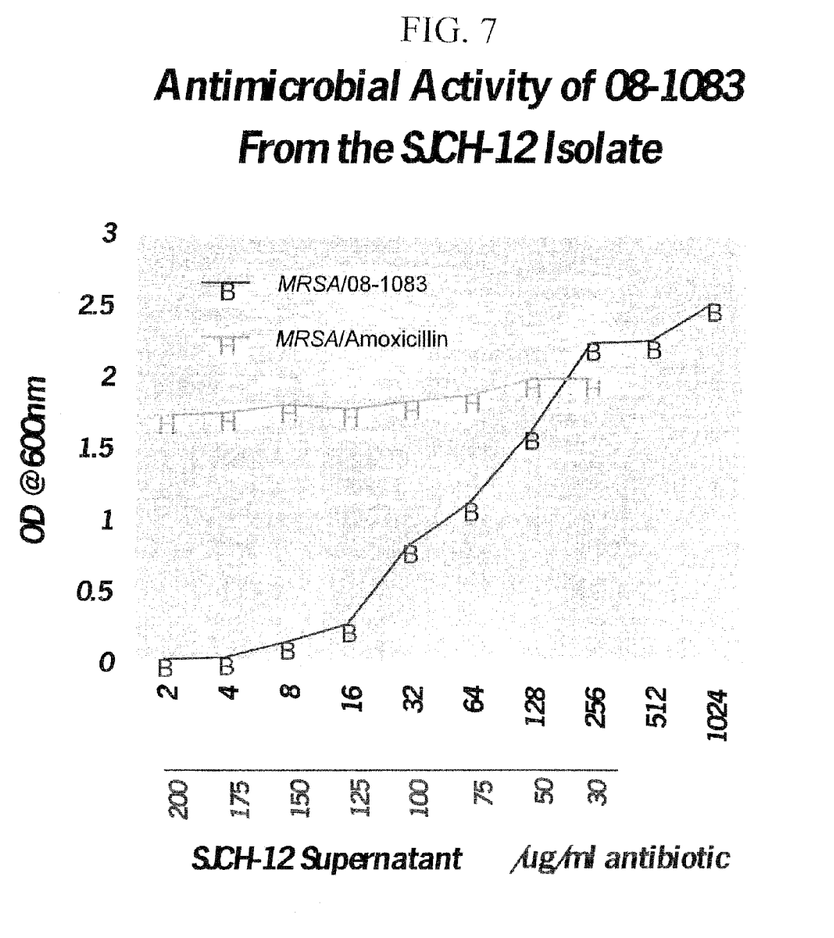
FIG. 7 shows activity of partially purified protein 08-1083 against MRSA compared with amoxicillin.
Figure 8:
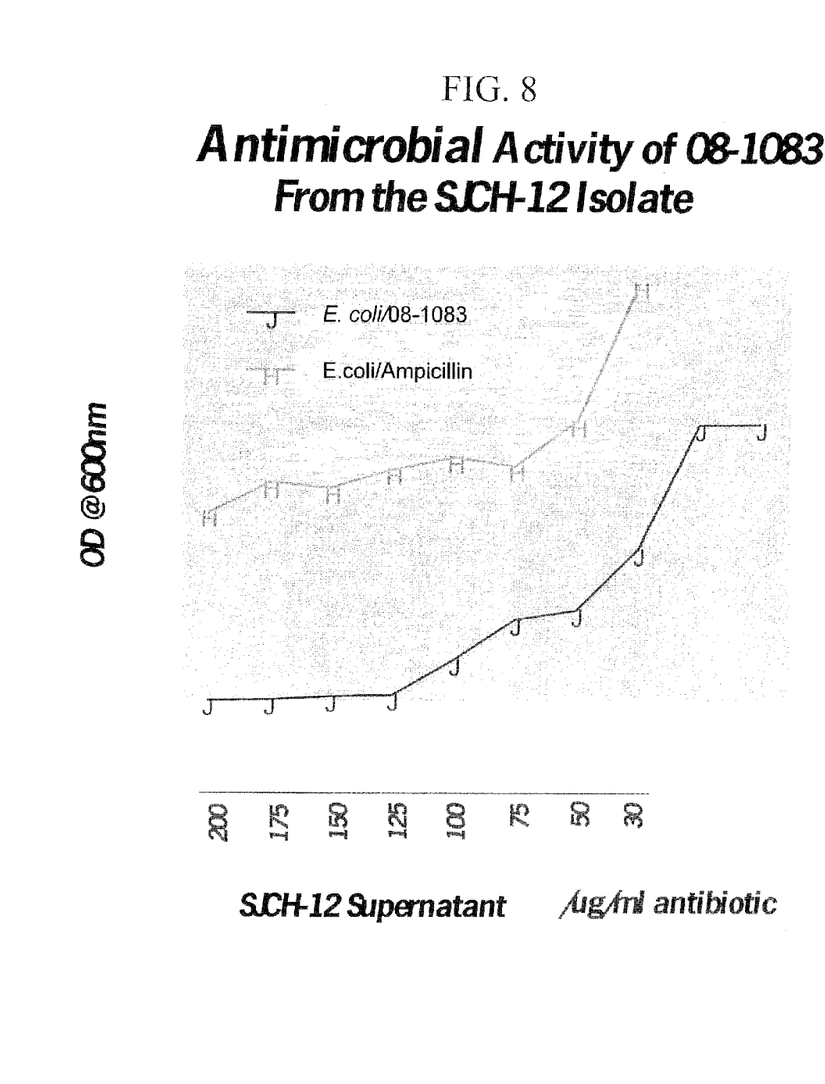
FIG. 8 shows activity of partially purified protein 08-1083 against *E. coli* compared with ampicillin.

The SJCH-12 bacteria appeared as Gram negative rods with a width of 0.7-0.8 microns and a length of 1.2-2.5 microns. They are anaerobic (facultative), acid producers (ASS), pigment producing (orange). No plasmid was detected and they are +/− with respect to hemolysin. FIG. 5 is a slide showing the rod shape.

The bacterial SJCH-12 cultures are stable at 4°, 25°, and 37° C. for at least 30 days and at 4° C. for at least 6 months. There is some loss of stability at 25° and 37° C. on 6 month storage.

Example 4

16S rRNA Gene Sequence of 08-1033 Bacteria

Approximately 95% of the 16S rRNA gene sequence of the SJCH-12 bacteria was determined by direct sequencing of PCR-amplified 16S rDNA, SEQ ID NO:1.

Genomic DNA extraction of bacterial strain SJCH-12 was followed by PCR mediated amplification of the 16S rDNA and purification of the PCR product as described by Rainey, et al. (1996). Purified PCR product was sequenced using the CEQTMDTCS-Quick Start Kit (Beckmann coulter) as directed in the manufacturer's protocol. Sequence reactions were electrophoresed using the CEQtm 8000 Genetic Analysis System.

Sequence data was put into the alignment editor ae2 and aligned manually. It was then compared with the 16S rRNA gene sequences of representative organisms belonging to the Enterobacteriaceae class.

Table 4 is a similarity matrix for SJCH-12 and a phylogenetic tree. The 16S rRNA gene similarity values were calculated by pairwise comparison of the sequences within the alignment. For construction of the phylogenetic dendrogram operations of the ARB package were used (Pruesse, et al., 2007). The phylogenetic tree was constructed by the neighbor-joining method using the correlation of Jukes and Cantor (196) based on the evolutionary distance values. The roots of the tree were determined by including the 16S rRNA gene sequence of *Cronobacter sakazakii* into the analysis. The scale bar below the dendrograms indicates the 1 nucleotide substitutions per 100 nucleotides.

The complete 16S rDNA gene sequence of strain SJCH-12 shows a highest similarity of 99.8% (binary value) with *Shigella sonnei*. On the basis of this result, strain SJCH-12 appears to represent at least one new species within the genus *Shigella*; however, the genus *Escherichia* is phylogenetically highly related to this genus; therefore, it cannot be excluded that strain SJCH-12 may also represent a new species within the genus *Escherichia*.

TABLE 4

| Strains | 1. | 2. | 3. | 4. | 5. | 6. | 7. | 8. | 9. | 10. | 11. |
|---|---|---|---|---|---|---|---|---|---|---|---|
| SJCH-12 (ID 08-1083) | — | | | | | | | | | | |
| *Escherichia albertii* LMG 20976[T] | 99.2 | — | | | | | | | | | |
| *Escherichia coli* ATCC 11775[T] | 99.6 | 99.2 | — | | | | | | | | |
| *Escherichia fergusonii* ATCC 35469[T] | 99.8 | 99.2 | 99.6 | — | | | | | | | |
| *Escherichia hermannii* GTC 347[T] | 97.4 | 96.8 | 97.1 | 97.4 | — | | | | | | |
| *Escherichia vulneris* ATCC 33821[T] | 99.7 | 99.1 | 99.5 | 99.7 | 97.2 | — | | | | | |
| *Shigella dysenteriae* ATCC 13313[T] | 98.9 | 98.3 | 98.7 | 98.9 | 97.3 | 98.8 | — | | | | |
| *Shigella flexneri* ATCC 29903[T] | 99.9 | 99.3 | 99.7 | 99.9 | 97.4 | 99.8 | 99.0 | — | | | |
| *Shigella sonnei* GTC 781[T] | 99.8 | 99.2 | 99.6 | 99.8 | 97.4 | 99.7 | 98.9 | 99.9 | — | | |
| *Salmonella bongori* BR 1859[T] | 97.3 | 97.1 | 97.1 | 97.3 | 97.7 | 97.1 | 97.9 | 97.4 | 97.3 | — | |
| *Salmonella enterica* ssp *arizonae* ATCC 13314[T] | 97.7 | 97.5 | 97.4 | 97.7 | 97.7 | 97.6 | 97.4 | 97.7 | 97.8 | 97.9 | — |
| *Brenneria alni* DSM 11811[T] | 93.1 | 92.6 | 92.9 | 93.0 | 93.5 | 92.9 | 93.1 | 93.0 | 93.1 | 93.4 | 93.5 |
| *Brenneria salicis* DSM 30166[T] | 93.0 | 92.5 | 92.8 | 93.1 | 93.5 | 92.9 | 93.3 | 93.1 | 93.0 | 93.5 | 93.2 |
| *Dickeya chrysanthemi* DSM 4610[T] | 95.0 | 94.2 | 94.6 | 94.8 | 94.1 | 94.8 | 95.0 | 94.9 | 94.8 | 94.8 | 94.8 |
| *Pectobacterium carotovorum* DSM 30168[T] | 95.0 | 94.5 | 95.0 | 95.0 | 95.6 | 94.9 | 95.3 | 95.0 | 95.0 | 95.8 | 95.4 |
| *Edwardsiella hoshinae* JCM1679[T] | 95.0 | 94.4 | 94.7 | 95.0 | 95.0 | 95.0 | 95.3 | 95.0 | 95.0 | 95.0 | 94.2 |
| *Edwardsiella ictaluri* JCM1680[T] | 95.2 | 94.5 | 94.9 | 95.1 | 95.0 | 95.1 | 95.4 | 95.2 | 95.1 | 95.2 | 94.4 |
| *Cedecea davisae* DSM 4568[T] | 96.5 | 95.9 | 96.2 | 96.5 | 97.7 | 96.5 | 96.4 | 96.5 | 96.5 | 96.2 | 96.2 |
| *Cedecea neteri* GTC1717[T] | 96.2 | 95.6 | 95.9 | 96.2 | 97.4 | 96.1 | 96.1 | 96.2 | 96.2 | 96.1 | 96.1 |

TABLE 4-continued

| | | | | | | | | | | |
|---|---|---|---|---|---|---|---|---|---|---|
| Trabulsiella guamensis ATCC 49490[T] | 95.5 | 94.9 | 95.3 | 95.6 | 96.4 | 95.6 | 96.1 | 95.6 | 95.5 | 96.2 | 96.0 |
| Cronobacter sakazakii ATCC 29544[T] | 96.8 | 96.8 | 96.6 | 96.9 | 96.7 | 96.8 | 97.0 | 96.9 | 96.8 | 96.5 | 96.5 |

| Strains | 12. | 13. | 14. | 15. | 16. | 17. | 18. | 19. | 20. | 21. |
|---|---|---|---|---|---|---|---|---|---|---|
| SJCH-12 (ID 08-1083) | | | | | | | | | | |
| Escherichia albertii LMG 20976[T] | | | | | | | | | | |
| Escherichia coli ATCC 11775[T] | | | | | | | | | | |
| Escherichia fergusonii ATCC 35469[T] | | | | | | | | | | |
| Escherichia hermannii GTC 347[T] | | | | | | | | | | |
| Escherichia vulneris ATCC 33821[T] | | | | | | | | | | |
| Shigella dysenteriae ATCC 13313[T] | | | | | | | | | | |
| Shigella flexneri ATCC 29903[T] | | | | | | | | | | |
| Shigella sonnei GTC 781[T] | | | | | | | | | | |
| Salmonella bongori BR 1859[T] | | | | | | | | | | |
| Salmonella enterica ssp arizonae ATCC 13314[T] | | | | | | | | | | |
| Brenneria alni DSM 11811[T] | | | | | | | | | | |
| Brenneria salicis DSM 30166[T] | 96.0 | — | | | | | | | | |
| Dickeya chrysanthemi DSM 4610[T] | 95.3 | 95.9 | — | | | | | | | |
| Pectobacterium carotovorum DSM 30168[T] | 95.6 | 94.7 | 96.2 | — | | | | | | |
| Edwardsiella hoshinae JCM1679[T] | 92.6 | 93.5 | 94.6 | 95.2 | — | | | | | |
| Edwardsiella ictaluri JCM1680[T] | 92.9 | 93.6 | 95.0 | 95.2 | 99.3 | — | | | | |
| Cedecea davisae DSM 4568[T] | 94.1 | 94.3 | 95.1 | 96.6 | 95.6 | 95.5 | — | | | |
| Cedecea neteri GTC1717[T] | 94.4 | 94.3 | 95.2 | 96.6 | 95.6 | 958 | 99.0 | — | | |
| Trabulsiella guamensis ATCC 49490[T] | 93.3 | 92.9 | 94.2 | 94.7 | 95.4 | 95.3 | 95.5 | 95.5 | — | |
| Cronobacter sakazakii ATCC 29544[T] | 93.0 | 93.7 | 95.0 | 94.7 | 95.5 | 95.3 | 96.3 | 95.3 | 96.8 | — |

Table 5 is the gene sequence (SEQ ID NO: 1) for the 16S rRNA for SJCH-12.

TABLE 5

```
LOCUS        1083-08      1530 bp      RNA          RNA          23-JAN-198
BASE COUNT   381 a        354 c        484 g        309 t        2 others

1   TTTGATCCTG  GCTCAGATTG  AACGCTGGCG  GCAGGCCTAA  CACATGCAAG  TCGAACGGTA

61   ACAGGAANCA  GCTTGCTGNT  TCGCTGACGA  GTGGCGGACG  GGTGAGTAAT  GTCTGGGAAA

121   CTGCCTGATG  GAGGGGGATA  ACTACTGGAA  ACGGTAGCTA  ATACCGCATA  ACGTCGCAAG

181   ACCAAAGAGG  GGGACCTTCG  GGCCTCTTGC  CATCGGATGT  GCCCAGATGG  GATTAGCTAG

241   TAGGTGGGGT  AAAGGCTCAC  CTAGGCGACG  ATCCCTAGCT  GGTCTGAGAG  GATGACCAGC

301   CACACTGGAA  CTGAGACACG  GTCCAGACTC  CTACGGGAGG  CAGCAGTGGG  GAATATTGCA

361   CAATGGGCGC  AAGCCTGATG  CAGCCATGCC  GCGTGTATGA  AGAAGGCCTT  CGGGTTGTAA

421   AGTACTTTCA  GCGGGGAGGA  AGGGAGTAAA  GTTAATACCT  TTGCTCATTG  ACGTTACCCG
```

TABLE 5-continued

```
 481 CAGAAGAAGC ACCGGCTAAC TCCGTGCCAG CAGCCGCGGT AATACGGAGG GTGCAAGCGT

541 TAATCGGAAT TACTGGGCGT AAAGCGCACG CAGGCGGTTT GTTAAGTCAG ATGTGAAATC

601 CCCGGGCTCA ACCTGGGAAC TGCATCTGAT ACTGGCAAGC TTGAGTCTCG TAGAGGGGGG

661 TAGAATTCCA GGTGTAGCGG TGAAATGCGT AGAGATCTGG AGGAATACCG GTGGCGAAGG

721 CGGCCCCCTG GACGAAGACT GACGCTCAGG TGCGAAAGCG TGGGGAGCAA ACAGGATTAG

781 ATACCCTGGT AGTCCACGCC GTAAACGATG TCGACTTGGA GGTTGTGCCC TTGAGGCGTG

841 GCTTCCGGAG CTAACGCGTT AAGTCGACCG CCTGGGGAGT ACGGCCGCAA GGTTAAAACT

901 CAAATGAATT GACGGGGGCC CGCACAAGCG GTGGAGCATG TGGTTTAATT CGATGCAACG

961 CGAAGAACCT TACCTGGTCT TGACATCCAC GGAAGTTTTC AGAGATGAGA ATGTGCCTTC

1021 GGGAACCGTG AGACAGGTGC TGCATGGCTG TCGTCAGCTC GTGTTGTGAA ATGTTGGGTT

1081 AAGTCCCGCA ACGAGCGCAA CCCTTATCCT TTGTTGCCAG CGGTCCGGCC GGGAACTCAA

1141 AGGAGACTGC CAGTGATAAA CTGGAGGAAG GTGGGGATGA CGTCAAGTCA TCATGGCCCT

1201 TACGACCAGG GCTACACACG TGCTACAATG GCGCATACAA AGAGAAGCGA CCTCGCGAGA

1261 GCAAGCGGAC CTCATAAAGT GCGTCGTAGT CCGGATTGGA GTCTGCAACT CGACTCCATG

1321 AAGTCGGAAT CGCTAGTAAT CGTGGATCAG AATGCCACGG TGAATACGTT CCCGGGCCTT

1381 GTACACACCG CCCGTCACAC CATGGGAGTG GGTTGCAAAA GAAGTAGGTA GCTTAACCTT

1441 CGGGAGGGCG CTTACCACTT TGTGATTCAT GACTGGGGTG AAGTCGTAAC AAGGTAACCG

1501 TAGGGAACC TGCGGCTGGA TCACCTCCTT
```

REFERENCES

Acebal, C., Canedo, L. M. Puentes, J. L. Fl, Baz, J. P., Romero, B., Da La Calle, and Rodrigues, M. 1999. Agrochelin, a new cytotoxic antivotice from a marine *agrobacterium*. Isolation, physiochemical properties and biological activity. J. Antibiotic. 52:983-987.

Biabani, M. A. F., Laatsch, H., Helmke, E., and Weyland, H. 1997. d-Indomycinone: class of antibiotics isolated from marine *Streptomyces* sp. J. Antibiot. 50: 874-877.

Gauthier, G., Gauthier, M. and Christen, R., 1995. Phylogenetic analysis of the genera and *Moritella* using genes coding for small-subunit rRNA sequence and division of the genera, *Alteromonas* (emended) and *Pseudoalteromonas* gen. November, and proposal of twel Int. J. Syst. Bacteriol. 45: 755-761.

Imamura, N., Nishijima, M. Takadera, T., Adachi, K., Sakai, M. and Sano, H. 1997. pelagiomicins produced by a new marine bacterium *Pelagiobacter variabilis*. J. Antibiot.

Pusecker, K., Laatsch, H., Helmke, E., and Weyland, H. 1997. dihydrophencomycin phenazine derivative from a marine Streptomycete. J. Antibiot. 50: 479-483.

Isnansetyo, A. and Kamei, Y. 2003. MC21-A, a Bactericidal Antibiotic Produced by a new Marine Bacterium *Pseudoalteromonas phenolica* sp. November O-BC30T, against Methicillin Resistant *Staphylococcus aureus*. Antimicrob. Agents chemother. February: 47(2) 48-488.

Usdin, S., BioCentury, Jun. 26, 2006.

Chemistry & Engineering News, Jan. 28, 2008, p. 57.

What is claimed is:

1. An isolated bacterial cell culture having Deutsche Sammlung von Mikroorganismen und Zellkulturen (DSMZ) accession number DSM 21971.

2. The bacterial cell culture of claim 1 comprising two species of bacteria.

3. The bacterial cell culture of claim 1 wherein one species of bacteria has a 16S RNA sequence comprising SEQ ID NO:1.

4. A kit comprising an isolated bacterial culture having Deutsche Sammlung von Mikroorganismen und Zellkulturen (DSMZ) accession number DSM 21971.

* * * * *

UNITED STATES PATENT AND TRADEMARK OFFICE
CERTIFICATE OF CORRECTION

| | | |
|---|---|---|
| PATENT NO. | : 8,114,657 B2 | Page 1 of 1 |
| APPLICATION NO. | : 13/060448 | |
| DATED | : February 14, 2012 | |
| INVENTOR(S) | : Michael J. P. Lawman, Selena Braccili and Shabnam Eidizadeh | |

It is certified that error appears in the above-identified patent and that said Letters Patent is hereby corrected as shown below:

Column 1,
Line 10, "tiled Aug. 24, 2009" should read --filed Aug. 24, 2009--.

Column 3,
Line 12, "Bulgula neritina" should read --Bugula neritina--.
Line 13, "phobol esters" should read --phorbol esters--.

Column 5,
Lines 32-33, "Braunschweig, Germany)Germany" should read
　　　　　--Braunschweig, Germany--.

Column 6,
Line 7, "SJCh-12" should read --SJCH-12--.

Column 9, Table 4,
Column 17, Row *Cedecea neteri* GTC1717$^T$, "958" should read --95.8--.

Column 12,
Line 35, "pelagiomicins" should read --Pelagiomicins--.
Line 37, "dihydrophencomycin" should read --Dihydrophencomycin--.
Line 40, "a Bactericidal" should read --A Bactericidal--.

Signed and Sealed this
Eighth Day of May, 2012

David J. Kappos
*Director of the United States Patent and Trademark Office*

UNITED STATES PATENT AND TRADEMARK OFFICE
CERTIFICATE OF CORRECTION

PATENT NO. : 8,114,657 B2
APPLICATION NO. : 13/060448
DATED : February 14, 2012
INVENTOR(S) : Michael J. P. Lawman, Selena Braccili and Shabnam Eidizadeh It is certified that error appears in the above-identified patent and that said Letters Patent is hereby corrected as shown below:

Cover Page, Item (73),
Assignee: "St. Joseph' Children' Hospital, Tampa, FL (US)" should read
--St. Joseph's Children's Hospital, Tampa, FL (US)--.

Signed and Sealed this
Third Day of July, 2012

David J. Kappos
*Director of the United States Patent and Trademark Office*

SEQUENCE LISTING

```
<160> NUMBER OF SEQ ID NOS: 1

<210> SEQ ID NO 1
<211> LENGTH: 1530
<212> TYPE: DNA
<213> ORGANISM: Pseudomonas stutzeri
<220> FEATURE:
<221> NAME/KEY: misc_feature
<222> LOCATION: (68)..(68)
<223> OTHER INFORMATION: n is a, c, g, or t
<220> FEATURE:
<221> NAME/KEY: misc_feature
<222> LOCATION: (79)..(79)
<223> OTHER INFORMATION: n is a, c, g, or t

<400> SEQUENCE: 1
```

```
tttgatcctg gctcagattg aacgctggcg gcaggcctaa cacatgcaag tcgaacggta      60
acaggaanca gcttgctgnt tcgctgacga gtggcggacg ggtgagtaat gtctgggaaa     120
ctgcctgatg gaggggggata actactggaa acgtagcta ataccgcata acgtcgcaag     180
accaaagagg gggaccttcg ggcctcttgc catcggatgt gcccagatgg gattagctag    240
taggtggggt aaaggctcac ctaggcgacg atccctagct ggtctgagag gatgaccagc    300
cacactggaa ctgagacacg gtccagactc ctacgggagg cagcagtggg gaatattgca    360
caatgggcgc aagcctgatg cagccatgcc gcgtgtatga agaaggcctt cgggttgtaa    420
agtactttca gcggggagga agggagtaaa gttaatacct ttgctcattg acgttacccg    480
cagaagaagc accggctaac tccgtgccag cagccgcggt aatacggagg gtgcaagcgt    540
taatcggaat tactgggcgt aaagcgcacg caggcggttt gttaagtcag atgtgaaatc    600
cccgggctca acctgggaac tgcatctgat actggcaagc ttgagtctcg tagaggggggg    660
tagaattcca ggtgtagcgg tgaaatgcgt agagatctgg aggaataccg gtggcgaagg    720
cggccccctg gacgaagact gacgctcagg tgcgaaagcg tggggagcaa acaggattag    780
ataccctggt agtccacgcc gtaaacgatg tcgacttgga ggttgtgccc ttgaggcgtg    840
gcttccggag ctaacgcgtt aagtcgaccg cctggggagt acggccgcaa ggttaaaact    900
caaatgaatt gacgggggcc cgcacaagcg gtggagcatg tggtttaatt cgatgcaacg    960
cgaagaacct tacctggtct tgacatccac ggaagttttc agagatgaga atgtgccttc    1020
gggaaccgtg agacaggtgc tgcatggctg tcgtcagctc gtgttgtgaa atgttgggtt    1080
aagtcccgca acgagcgcaa cccttatcct ttgttgccag cggtccggcc gggaactcaa    1140
aggagactgc cagtgataaa ctggaggaag gtggggatga cgtcaagtca tcatggccct    1200
tacgaccagg gctacacacg tgctacaatg gcgcatacaa agagaagcga cctcgcgaga    1260
gcaagcggac ctcataaagt gcgtcgtagt ccggattgga gtctgcaact cgactccatg    1320
aagtcggaat cgctagtaat cgtggatcag aatgccacgg tgaatacgtt cccgggcctt    1380
gtacacaccg cccgtcacac catgggagtg ggttgcaaaa gaagtaggta gcttaacctt    1440
cgggagggcg cttaccactt tgtgattcat gactggggtg aagtcgtaac aaggtaaccg    1500
tagggggaacc tgcggctgga tcacctcctt                                    1530
```